United States Patent [19]

Jablonski et al.

[11] Patent Number: 5,396,016

[45] Date of Patent: Mar. 7, 1995

[54] MCM-36 AS A CATALYST FOR UPGRADING PARAFFINS

[75] Inventors: Gregory A. Jablonski, Rose Valley, Pa.; David O. Marler, Deptford; Wieslaw J. Roth, Sewell, both of N.J.

[73] Assignee: Mobil Oil Corp., Fairfax, Va.

[21] Appl. No.: 108,258

[22] Filed: Aug. 19, 1993

[51] Int. Cl.⁶ ............................................. C07C 5/52
[52] U.S. Cl. .................................. 585/708; 585/739
[58] Field of Search ............................. 585/739, 708

[56] References Cited

U.S. PATENT DOCUMENTS

| | | | |
|---|---|---|---|
| 3,893,942 | 7/1975 | Yang | 585/722 |
| 4,686,316 | 8/1987 | Morrison | 585/708 |
| 4,754,100 | 6/1988 | Sorensen et al. | 585/708 |
| 4,929,793 | 5/1990 | Morrison | 585/708 |
| 5,107,054 | 4/1992 | Del Rossi et al. | 585/739 |
| 5,171,912 | 12/1992 | Harandi | 585/301 |
| 5,250,277 | 10/1993 | Kresge et al. | 423/329.1 |

*Primary Examiner*—Anthony McFarlane
*Attorney, Agent, or Firm*—Alexander J. McKillop; Dennis P. Santini; Edward F. Kenehan, Jr.

[57] ABSTRACT

There is provided a process for isomerizing and/or disproportionating a paraffin over a catalyst comprising MCM-36. Examples of paraffins which may be isomerized and/or disproportionated include those having from 3 to 10 carbon atoms. The reaction may take place in the presence or absence of cofed hydrogen, and the catalyst may optionally include a hydrogenation metal, such as platinum. An example of a particular reaction is the disproportionation of isopentane to produce a product comprising isobutane and branched hexanes.

12 Claims, 2 Drawing Sheets

MCM-36 AS A CATALYST FOR UPGRADING PARAFFINS

CROSS REFERENCE TO RELATED APPLICATIONS

This application is related to copending U.S. application Ser. No. 07/811,360, filed Dec. 20, 1991, now U.S. Pat. No. 5,250,277, which is a continuation-in-part of copending U.S. application Ser. No. 07/776,718, filed Oct. 15, 1991, now abandoned, which is a continuation of U.S. application Ser. No. 07/640,330, filed Jan. 11, 1991, now abandoned.

BACKGROUND

The present invention relates to a process for upgrading feedstocks containing paraffins. This process involves isomerization and/or disproportionation over a catalyst comprising MCM-36. Paraffin isomerization may involve skeletal rearrangement of low octane linear paraffins and only slightly branched paraffins to higher octane, more highly branched paraffins. Paraffin disproportionation involves converting paraffins to other paraffins containing at least one more and at least one less carbon fragment per molecule. In the present process, paraffins produced by disproportionation tend to have a large degree of branching.

A unit process which is frequently encountered in petroleum refining is paraffin isomerization. Paraffin isomerization of linear (straight chain) paraffins produces branched chain paraffins. In such a process, as conventionally operated, low molecular weight $C_4$–$C_6$ paraffins are converted to iso-paraffins in the presence of an acidic catalyst such as chlorided alumina. Recently, $C_6+$, preferably $C_{10}+$ n-paraffins, have been isomerized, in the presence of large pore size zeolites to produce branched chain paraffins by skeletal rearrangement. The latter process can find application in dewaxing.

Isomerization is one of several reactions which occur in reforming of naphthas. Reforming of naphthas is undertaken to upgrade a low octane naphtha to a higher octane effluent. One of the octane enhancing reactions which occurs during reforming is the isomerization of n-paraffins to isoparaffins. Under the process conditions of reforming, other reactions which occur are aromatization (or dehydrocyclization), dehydrogenation, with some cracking.

Paraffin isomerization catalysts may also be employed as ring opening catalysts for removal of cyclic aromatic precursors from reformer feedstocks. For example, cyclohexane, a precursor to benzene, is rearranged over commercial paraffin isomerization catalysts to a mixture of branched paraffins. Branched paraffins are only partly aromatized in reforming whereas cyclohexane is completely converted to aromatics, mostly benzene. Application of paraffin isomerization catalysts for ring opening aromatics precursors will no doubt become more important as environmental regulations limiting aromatics in gasoline become more stringent.

U.S. Pat. No. 5,107,054 describes the use of a zeolite, designated MCM-22, to catalyze the isomerization of certain paraffins, such as those included in a low octane, light straight run naphtha.

Zeolite catalyzed paraffin disproportionation reactions are described in a number of U.S. Patents. U.S. Pat. No. 3,914,331 describes the use of ZSM-4 to catalyze the disproportionation of certain paraffins including pentane and hexane.

U.S. Pat. No. 3,953,537 describes the use of certain large pore size zeolites, such as synthetic faujasite, to catalyze the disproportionation of certain paraffins, such as propane, butane and pentane.

U.S. Pat. No. 4,686,316 describes the use of certain medium pore size zeolites, such as ZSM-5, to catalyze the conversion of propane to a product comprising isobutane.

U.S. Pat. No. 4,929,793 describes the use of certain medium pore size zeolites, such as ZSM-5, to catalyze the disproportionation of certain paraffins, such as those included in a $C_5$ to $C_9$ UDEX raffinate.

U.S. Pat. No. 5,171,912 describes the use of certain medium pore size zeolites, such as ZSM-5 and MCM-22, to catalyze the disproportionation of propane and butane.

SUMMARY

There is provided a process for isomerizing and/or disproportionating a paraffin, said process comprising contacting said paraffin with a catalyst comprising MCM-36, said contacting taking place under conditions sufficient to cause (i) an isomerization reaction involving skeletal rearrangement of said paraffin to an isomer thereof having the same number of carbon atoms, or (ii) a disproportionation reaction involving conversion of said paraffin to other paraffins having at least one more and at least one less carbon atom per molecule, or (iii) both said isomerization reaction and said disproportionation reaction. The paraffins which are isomerized and/or disproportionated by the present process may have from 3 to 10 carbon atoms.

EMBODIMENTS

Figure 1:
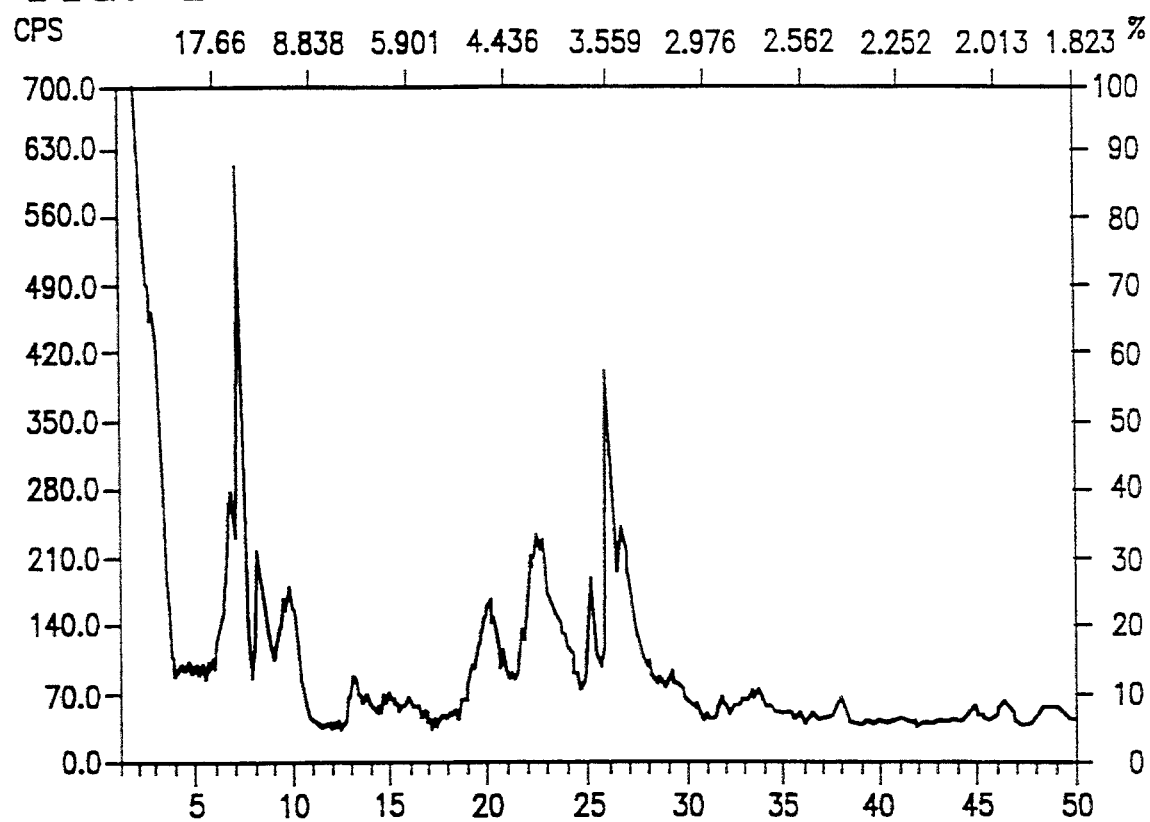
FIG. 1 is an X-ray diffraction pattern of an assynthesized form of a layered material which may be swollen and pillared.

The catalytic isomerization/disproportionation process described herein may be used to increase the octane and reduce the vapor pressure of low octane naphthas containing $C_6$–$C_{10}$ n-paraffins and/or mono-methyl branched paraffins, which under conventional reforming conditions, are the most difficult components to upgrade. The present process may minimize, if not eliminate, the cracking of $C_5+$ hydrocarbons which include $C_6$–$C_{10}$ n-paraffins. Particular uses of the present isomerization/disproportionation process are for upgrading refinery streams rich in $C_4$–$C_6$ n-paraffins.

In accordance with an embodiment described herein, isomerization and/or disproportionation are undertaken in the presence of a catalyst comprising a dehydrogenation/hydrogenation metal and a material designated MCM-36. During the isomerization, n-paraffinic and mono-methyl branched paraffinic components are isomerized to higher branched paraffins which are generally better octane boosters. The product of disproportionation also contains a relatively large degree of branching. By way of illustration, the significance of these reactions can be gleaned from a review of the following table of octane numbers of pure hydrocarbons from *Catalysis*, P. H. Emmett (ed.), vol. VI (1958).

Octane Numbers of Pure Hydrocarbons

| Hydrocarbon | Blending Research Octane Number (clear) |
|---|---|
| Paraffins | |
| n-heptane | 0 |
| 2-methylhexane | 41 |
| 3-methylhexane | 56 |
| 2,2-dimethylpentane | 89 |
| 2,3-dimethylpentane | 87 |
| 2,2,3-trimethylbutane | 113 |

The feedstock for the present process may contain significant amounts of $C_5+$ normal and/or slightly branched paraffins, especially normal and/or slightly branched paraffins in the $C_6$–$C_{10}$ range. Accordingly, normal hexane and normal heptane as well as the various mono-methyl branched isomers alone or in admixture may be employed as the feedstock in the present process. In addition, the feedstock may contain monocyclic aromatic compounds and/or cyclic paraffins, such as cyclohexane.

The feedstock to the present isomerization/disproportionation process can be straight-run, thermal, or catalytically cracked naphtha. Typically, naphthas boil at 80° to 400° F. Preferably, for high increases in octane numbers of the feed, the charge to the process is a naphtha rich in $C_6$ to $C_{10}$ paraffins. Naphtha rich in $C_6$ and $C_7$ paraffins is generally difficult to reform selectively using conventional catalysts (such as chlorided Pt-alumina). Naphthas can be obtained by separating the charge into two fractions: a light naphtha and a heavy naphtha. Conventionally such separation is by distillation. The boiling range of the light naphtha may be from about 80° F. to about 400° F. and the boiling range of the heavy naphtha may include up to about 650° F. The light naphtha may be rich in $C_6$–$C_{10}$ paraffins, and specifically $C_6$ and $C_7$ paraffins. When the light naphtha is upgraded in accordance with the present process, the heavy naphtha may be processed by conventional reforming.

Generally, the feeds for the present process do not contain bicyclic and polycyclic aromatics. Bicyclic and polycyclic aromatics are commonly found in the higher boiling fractions (IBP over 340° C.), than those which are generally used as feeds in the process of the invention. Single ring (monocyclic) aromatics which are readily hydrogenated over an optional metal component of the catalyst can be tolerated, and at the higher end of the range of temperature conditions of the present process may be subject to ring opening to form branched chain paraffin compounds. The aromatic content may, for preference, be held below 10 weight percent although slightly greater amounts up to about 30 weight percent might be tolerated if the proportion of monocyclic aromatics is sufficiently high and if a sufficiently strong hydrogenation component such as platinum is present on the catalyst.

The feed may, optionally, be pretreated in an aromatics saturator prior to contact with the present catalyst. Aromatics, such as benzene, may be hydrogenated to form saturated cyclics, such as cyclohexane, when reacted with hydrogen over a non-acidic, hydrogenation catalyst, such as platinum on amorphous alumina, in an aromatics saturator reactor.

The feedstock may be a refinery stream which contains significant amounts of $C_4$–$C_6$ n-paraffins.

Catalyst

The catalyst composition employed in the present process comprises an optional dehydrogenation/hydrogenation component and MCM-36.

MCM-36 and methods for its preparation are described in the aforementioned U.S. application Ser. No. 07/811,360, filed Dec. 20, 1991, now U.S. Pat. No. 5,250,277, the entire disclosure of which is expressly incorporated herein by reference.

MCM-36 may be prepared from an intermediate material which is crystallized in the presence of a hexamethyleneimine directing agent and which, if calcined without being swollen, would be transformed into a material having an X-ray diffraction pattern as shown in Table 1.

TABLE 1

| Interplanar d-Spacing (A) | Relative Intensity, $I/I_o \times 100$ |
|---|---|
| 30.0 ± 2.2 | w–m |
| 22.1 ± 1.3 | w |
| 12.36 ± 0.2 | m–vs |
| 11.03 ± 0.2 | m–s |
| 8.83 ± 0.14 | m–vs |
| 6.86 ± 0.14 | w–m |
| 6.18 ± 0.12 | m–vs |
| 6.00 ± 0.10 | w–m |
| 5.54 ± 0.10 | w–m |
| 4.92 ± 0.09 | w |
| 4.64 ± 0.08 | w |
| 4.41 ± 0.08 | w–m |
| 4.25 ± 0.08 | w |
| 4.10 ± 0.07 | w–s |
| 4.06 ± 0.07 | w–s |
| 3.91 ± 0.07 | m–vs |
| 3.75 ± 0.06 | w–m |
| 3.56 ± 0.06 | w–m |
| 3.42 ± 0.06 | vs |
| 3.30 ± 0.05 | w–m |
| 3.20 ± 0.05 | w–m |
| 3.14 ± 0.05 | w–m |
| 3.07 ± 0.05 | w |
| 2.99 ± 0.05 | w |
| 2.82 ± 0.05 | w |
| 2.78 ± 0.05 | w |
| 2.68 ± 0.05 | w |
| 2.59 ± 0.05 | w |

The values in this Table and like tables presented hereinafter were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables 1–8, the relative intensities are given in terms of the symbols w=weak, m=medium, s=strong and vs=very strong. In terms of intensities, these may be generally designated as follows:

w=0–20
m=20–40
s=40–60 vs = 60–100

The material having the X-ray diffraction pattern of Table 1 is known as MCM-22 and is described in U.S. Pat. No. 4,954,325, the entire disclosure of which is incorporated herein by reference. This material can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–80 | 10–60 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In the synthesis method for preparing the material having the X-ray diffraction pattern of Table 1, the source of $YO_2$ must be comprised predominately of solid $YO_2$, for example at least about 30 wt. % solid $YO_2$ in order to obtain the desired crystal product. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method taught in U.S. Pat. No. 4,439,409. If another source of oxide of silicon e.g., Q-Brand (a sodium silicate comprised of about 28.8 wt. % $SiO_2$, 8.9 wt. % $Na_2O$ and 62.3 wt. % $H_2O$) is used, crystallization yields little or none of the crystalline material having the X-ray diffraction pattern of Table 1. Impurity phases of other crystal structures, e.g., ZSM-12, are prepared in the latter circumstance. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the crystalline material having the X-ray diffraction pattern of Table 1 can be carried out at either static or stirred conditions in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g., from about 24 hours to about 60 days. Thereafter, the crystals are separated from the liquid and recovered.

The organic directing agent for use in synthesizing the present crystalline material from the above reaction mixture may be hexamethyleneimine which has the following structural formula:

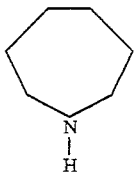

Other organic directing agents which may be used include 1,4-diazacycloheptane, azacyclooctane, aminocyclohexane, aminocycloheptane, aminocyclopentane, N,N,N-trimethyl-1-adamantanammonium ions, and N,N,N-trimethyl-2-adamantanammonium ions. In general, the organic directing agent may be selected from the group consisting of heterocyclic imines, cycloalkyl amines and adamantine quaternary ammonium ions.

It should be realized that the reaction mixture components can be supplied by more than one source. The reaction mixture can be prepared either batchwise or continuously. Crystal size and crystallization time of the crystalline material will vary with the nature of the reaction mixture employed and the crystallization conditions.

Synthesis of crystals may be facilitated by the presence of at least 0.01 percent, e.g., 0.10 percent or 1 percent, seed crystals (based on total weight) of crystalline product.

The crystalline material having the X-ray diffraction pattern of Table 1 passes through an intermediate stage. The material at this intermediate stage has a different X-ray diffraction pattern than that set forth in Table 1. It has further been discovered that this intermediate material is swellable with the use of suitable swelling agents such as cetyltrimethylammonium compounds, e.g., cetyltrimethylammonium hydroxide. However, when this swollen intermediate material is calcined, even under mild conditions, whereby the swelling agent is removed, the material can no longer be swollen with such swelling agent. By way of contrast it is noted that various layered silicates such as magadiite and kenyaite may be swellable with cetyltrimethylammonium compounds both prior to and after mild calcination.

The present swollen products may have relatively high interplanar distance (d-spacing), e.g., greater than about 6 Angstrom, e.g., greater than about 10 Angstrom and even exceeding 30 Angstrom. These swollen materials may be converted into pillared materials. These pillared materials, particularly silica pillared materials, may be capable of being exposed to severe conditions such as those encountered in calcining, e.g., at temperatures of about 450° C. for about two or more hours, e.g., four hours, in nitrogen or air, without significant decrease, e.g., less than about 10%, in interlayer distance.

The material having the X-ray diffraction pattern of Table 1, when intercepted in the swellable, intermediate state, prior to final calcination, may have the X-ray diffraction pattern shown in Table 2.

TABLE 2

| d (A) | $I/I_o$ |
|---|---|
| 13.53 ± 0.2 | m–vs |
| 12.38 ± 0.2 | m–vs |
| 11.13 ± 0.2 | w–s |
| 9.15 ± 0.15 | w–s |
| 6.89 ± 0.15 | w–m |
| 4.47 ± 0.10 | w–m |
| 3.95 ± 0.08 | w–vs |
| 3.56 ± 0.06 | w–m |

TABLE 2-continued

| d (A) | I/I$_o$ |
| --- | --- |
| 3.43 ± 0.06 | m-vs |
| 3.36 ± 0.05 | w-s |

An X-ray diffraction pattern trace for an example of such an as-synthesized, swellable material is shown in FIG. 1. A particular example of such an as-synthesized, swellable material is the material of Example 1 of the aforementioned U.S. Pat. No. 4,954,325. This material of Example 1 of U.S. Pat. No. 4,954,325 has the X-ray diffraction pattern given in the following Table 3.

TABLE 3

| 2 Theta | d(A) | I/I × 100 |
| --- | --- | --- |
| 3.1 | 28.5 | 14 |
| 3.9 | 22.7 | <1 |
| 6.53 | 13.53 | 36 |
| 7.14 | 12.38 | 100 |
| 7.94 | 11.13 | 34 |
| 9.67 | 9.15 | 20 |
| 12.85 | 6.89 | 6 |
| 13.26 | 6.68 | 4 |
| 14.36 | 6.17 | 2 |
| 14.70 | 6.03 | 5 |
| 15.85 | 5.59 | 4 |
| 19.00 | 4.67 | 2 |
| 19.85 | 4.47 | 22 |
| 21.56 | 4.12 | 10 |
| 21.94 | 4.05 | 19 |
| 22.53 | 3.95 | 21 |
| 23.59 | 3.77 | 13 |
| 24.98 | 3.56 | 20 |
| 25.98 | 3.43 | 55 |
| 26.56 | 3.36 | 23 |
| 29.15 | 3.06 | 4 |
| 31.58 | 2.833 | 3 |
| 32.34 | 2.768 | 2 |
| 33.48 | 2.676 | 5 |
| 34.87 | 2.573 | 1 |
| 36.34 | 2.472 | 2 |
| 37.18 | 2.418 | 1 |
| 37.82 | 2.379 | 5 |

Taking into account certain modifications, this swellable material may be swollen and pillared by methods generally discussed in the aforementioned U.S. Pat. No. 4,859,648, the entire disclosure of which is expressly incorporated herein be reference. The present modifications are discussed hereinafter and include the selection of proper swelling pH and swelling agent.

Upon being swollen with a suitable swelling agent, such as a cetyltrimethylammonium compound, the swollen material may have the X-ray diffraction pattern shown in Table 4.

TABLE 4

| d(A) | I/I$_o$ |
| --- | --- |
| >32.2 | vs |
| 12.41 ± 0.25 | w-s |
| 3.44 ± 0.07 | w-s |

The X-ray diffraction pattern of this swollen material may have additional lines with a d(A) spacing less than the line at 12.41±0.25, but none of said additional lines have an intensity greater than the line at the d(A) spacing of 12.41±0.25 or at 3.44±0.07, whichever is more intense. More particularly, the X-ray diffraction pattern of this swollen material may have the lines shown in the following Table 5.

TABLE 5

| d(A) | I/I$_o$ |
| --- | --- |
| >32.2 | vs |
| 12.41 ± 0.25 | w-s |
| 11.04 ± 0.22 | w |
| 9.28 ± 0.19 | w |
| 6.92 ± 0.14 | w |
| 4.48 ± 0.09 | w-m |
| 3.96 ± 0.08 | w-m |
| 3.57 ± 0.07 | w-m |
| 3.44 ± 0.07 | w-s |
| 3.35 ± 0.07 | w |

Even further lines may be revealed upon better resolution of the X-ray diffraction pattern. For example, the X-ray diffraction pattern may have additional lines at the following d(A) spacings (intensities given in parentheses): 16.7±4.0 (w-m); 6.11±0.24 (w); 4.05±0.08 (w); and 3.80±0.08 (w).

In the region with d<9 A, the pattern for the swollen material is essentially like the one given in Table 2 for the unswollen material, but with the possibility of broadening of peaks.

Figure 2:
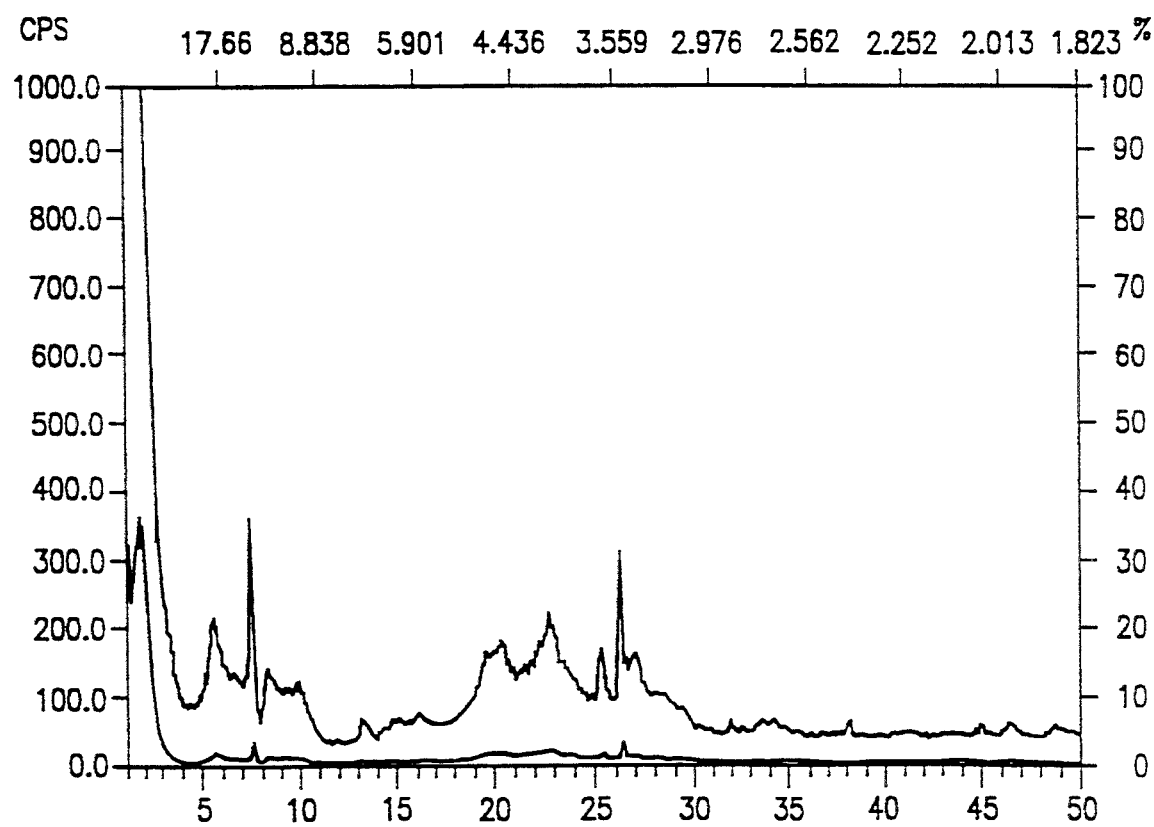
FIG. 2 is an X-ray diffraction pattern of a swollen form of the material having the X-ray diffraction pattern shown in FIG. 1.

An X-ray diffraction pattern trace for an example of such a swollen material is shown in FIG. 2. The upper profile is a 10-fold magnification of the lower profile in FIG. 2.

Upon being pillared with a suitable polymeric oxide, such as polymeric silica, the swollen material having the X-ray diffraction pattern shown in Table 4 may be converted into a material having the X-ray diffraction pattern shown in Table 6.

TABLE 6

| d(A) | I/I$_o$ |
| --- | --- |
| >32.2 | vs |
| 12.38 ± 0.25 | w-m |
| 3.42 ± 0.07 | w-m |

The X-ray diffraction pattern of this pillared material may have additional lines with a d(A) spacing less than the line at 12.38±0.25, but none of said additional lines have an intensity greater than the line at the d(A) spacing of 12.38±0.25 or 3.42±0.07, whichever is more intense. More particularly, the X-ray diffraction pattern of this pillared material may have the lines shown in the following Table 7.

TABLE 7

| d(A) | I/I$_o$ |
| --- | --- |
| >32.2 | vs |
| 12.38 ± 0.25 | w-m |
| 10.94 ± 0.22 | w-m |
| 9.01 ± 0.18 | w |
| 6.88 ± 0.14 | w |
| 6.16 ± 0.12 | w-m |
| 3.93 ± 0.08 | w-m |
| 3.55 ± 0.07 | w |
| 3.42 ± 0.07 | w-m |
| 3.33 ± 0.07 | w-m |

Even further lines may be revealed upon better resolution of the X-ray diffraction pattern. For example, the X-ray diffraction pattern may have additional lines at the following d(A) spacings (intensities given in parentheses): 5.59±0.11 (w); 4.42±0.09 (w); 4.11±0.08 (w); 4.04±0.08 (w); and 3.76±0.08 (w).

Figure 3:
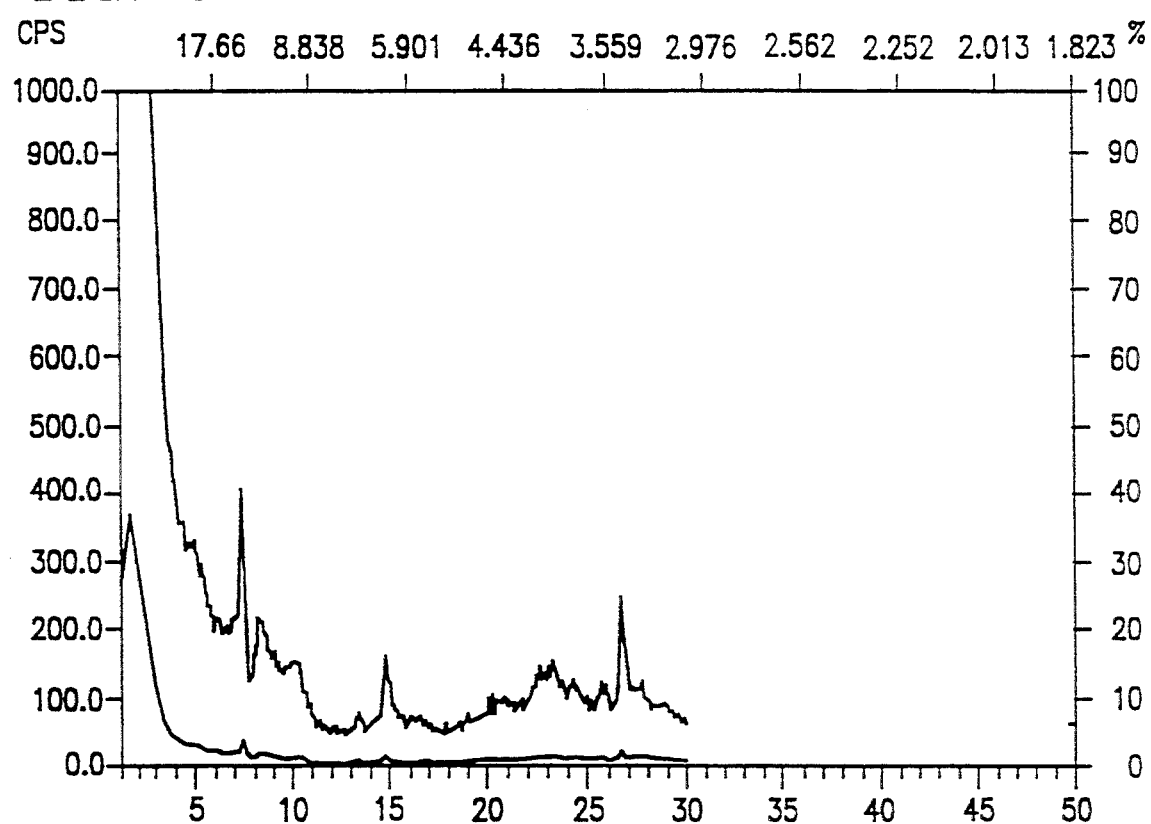
FIG. 3 is an X-ray diffraction pattern of the pillared form of the layered material having the X-ray diffraction pattern shown in FIG. 1.

An X-ray diffraction pattern trace for an example of such a pillared material is given in FIG. 3. The upper profile is a 10-fold magnification of the lower profile in FIG. 3.

If the material swollen with a suitable swelling agent is calcined without prior pillaring another material is produced. For example, if the material which is swollen but not pillared is calcined in air for 6 hours at 540° C., a very strong line at a d(A) spacing of greater than 32.2 will no longer be observed. By way of contrast, when the swollen, pillared material is calcined in air for 6 hours at 540° C., a very strong line at a d(A) spacing of greater than 32.2 will still be observed, although the precise position of the line may shift.

An example of a swollen, non-pillared material, which has been calcined, has the pattern as shown in Table 8.

TABLE 8

| 2 Theta | d(A) | $I/I_o \times 100$ | |
|---|---|---|---|
| 3.8 | 23.3 | 12 | |
| 7.02 | 12.59 | 100 | |
| 8.02 | 11.02 | 20 | |
| 9.66 | 9.16 | 14 | |
| 12.77 | 6.93 | 7 | |
| 14.34 | 6.18 | 45 | |
| 15.75 | 5.63 | 8 | |
| 18.19 | 4.88 | 3 | |
| 18.94 | 4.69 | 3 | |
| 19.92 | 4.46 | 13 | broad |
| 21.52 | 4.13 | 13 | shoulder |
| 21.94 | 4.05 | 18 | |
| 22.55 | 3.94 | 32 | |
| 23.58 | 3.77 | 16 | |
| 24.99 | 3.56 | 20 | |
| 25.94 | 3.43 | 61 | |
| 26.73 | 3.33 | 19 | |
| 31.60 | 2.831 | 3 | |
| 33.41 | 2.682 | 4 | |
| 34.62 | 2.591 | 3 | broad |
| 36.36 | 2.471 | 1 | |
| 37.81 | 2.379 | 4 | |

The X-ray powder pattern shown in Table 8 is similar to that shown in Table 1 except that most of the peaks in Table 8 are much broader than those in Table 1.

Figure 4:
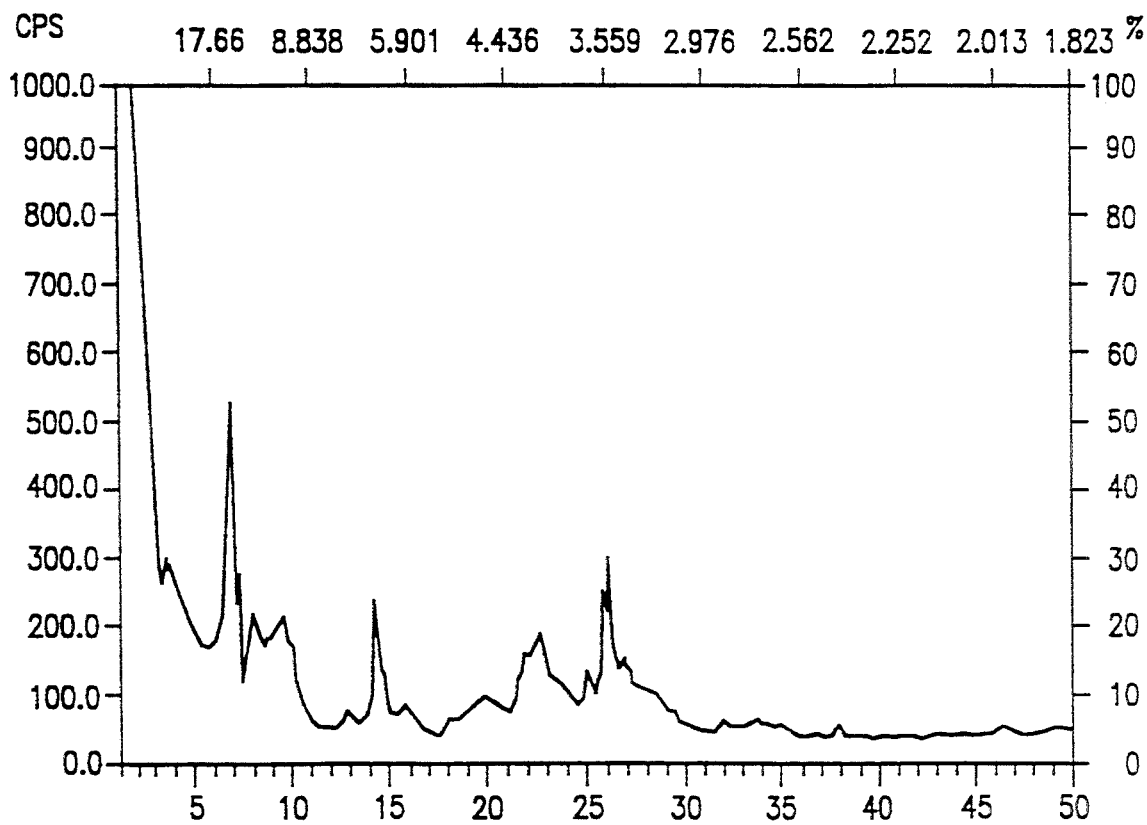
FIG. 4 is an X-ray diffraction pattern of the calcined form of the swollen material having the X-ray diffraction pattern shown in FIG. 2.

An X-ray diffraction pattern trace for an example of the calcined material corresponding to Table 8 is given in FIG. 4.

As mentioned previously, the calcined material corresponding to the X-ray diffraction pattern of Table 1 is designated MCM-22. For the purposes of the present disclosure, the pillared material corresponding to the X-ray diffraction pattern of Table 6 is designated herein as MCM-36. The swollen material corresponding to the X-ray diffraction pattern of Table 4 is designated herein as the swollen MCM-22 precursor. The as-synthesized material corresponding to the X-ray diffraction pattern of Table 2 is referred to herein, simply, as the MCM-22 precursor.

The layers of the swollen material of this disclosure may have a composition involving the molar relationship:

$X_2O_3:(n)YO_2$, wherein X is a trivalent element, such as aluminum, boron, iron and/or gallium, preferably aluminum, Y is a tetravalent element such as silicon and/or germanium, preferably silicon, and n is at least about 5, usually from about 10 to about 150, more usually from about 10 to about 60, and even more usually from about 10 to about 40.

To the extent that the layers of the swollen MCM-22 precursor and MCM-36 have negative charges, these negative charges are balanced with cations. For example, expressed in terms of moles of oxides, the layers of the swollen MCM-22 precursor and MCM-36 may have a ratio of 0.5 to 1.5 $R_2O:X_2O_3$, where R is a monovalent cation or 1/m of a cation of valency m.

MCM-36 adsorbs significant amounts of commonly used test adsorbate materials, i.e., cyclohexane, n-hexane and water. Adsorption capacities for this pillared material, especially the silica pillared material, may range at room temperature as follows:

| Adsorbate | Capacity, Wt. Percent |
|---|---|
| n-hexane | 17–40 |
| cyclohexane | 17–40 |
| water | 10–40 | wherein cyclohexane and n-hexane sorption are measured at 20 Torr and water sorption is measured at 12 Torr.

The swellable material, used to form the swollen material of the present disclosure, may be initially treated with a swelling agent. Such swelling agents are materials which cause the swellable layers to separate by becoming incorporated into the interspathic region of these layers. The swelling agents are removable by calcination, preferably in an oxidizing atmosphere, whereby the swelling agent becomes decomposed and/or oxidized.

Suitable swelling agents may comprise a source of organic cation, such as quaternary organoammonium or organophosphonium cations, in order to effect an exchange of interspathic cations. Organoammonium cations, such as n-octylammonium, showed smaller swelling efficiency than, for example, cetyltrimethylammonium. A pH range of 11 to 14, preferably 12.5 to 13.5 is generally employed during treatment with the swelling agent.

The as-synthesized material is preferably not dried prior to being swollen. This as-synthesized material may be in the form of a wet cake having a solids content of less than 30% by weight, e.g., 25wt % or less.

The foregoing swelling treatment results in the formation of a layered oxide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. When contact of the layered oxide with the swelling agent is conducted in aqueous medium, water is trapped between the layers of the swollen species.

The organic-swollen species may be treated with a compound capable of conversion, e.g., by hydrolysis and/or calcination, to pillars of an oxide, preferably to a polymeric oxide. Where the treatment involves hydrolysis, this treatment may be carried out using the water already present in organic-swollen material. In this case, the extent of hydrolysis may be modified by varying the extent to which the organic-swollen species is dried prior to addition of the polymeric oxide precursor.

It is preferred that the organic cation deposited between the layers be capable of being removed from the pillared material without substantial disturbance or removal of the interspathic polymeric oxide. For example, organic cations such as cetyltrimethylammonium may be removed by exposure to elevated temperatures, e.g., calcination, in nitrogen or air, or by chemical oxidation preferably after the interspathic polymeric oxide precursor has been converted to the polymeric oxide pillars in order to form the pillared layered product.

These pillared layered products, especially when calcined, exhibit high surface area, e.g., greater than 500 $m^2/g$, and thermal and hydrothermal stability making them highly useful as catalysts or catalytic supports, for hydrocarbon conversion processes, for example, alkylation.

Insertion of the organic cation between the adjoining layers serves to physically separate the layers in such a way as to make the layered material receptive to the interlayer addition of a polymeric oxide precursor. In particular, cetyltrimethylammonium cations have been found useful. These cations are readily incorporated within the interlayer spaces of the layered oxide serving to prop open the layers in such a way as to allow incorporation of the polymeric oxide precursor. The extent of the interlayer spacing can be controlled by the size of the organoammonium ion employed.

Interspathic oxide pillars, which may be formed between the layers of the propped or swollen oxide material, may include an oxide, preferably a polymeric oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other suitable oxides include those of Group VA, e.g., V, Nb, and Ta, those of Group IIA, e.g., Mg or those of Group IIIB, e.g., B. Most preferably, the pillars include polymeric silica. In addition, the oxide pillars may include an element which provides catalytically active acid sites in the pillars, preferably aluminum.

The oxide pillars are formed from a precursor material which may be introduced between the layers of the organic "propped" species as an ionic or electrically neutral compound of the desired elements, e.g., those of Group IVB. The precursor material may be an organometallic compound which is a liquid under ambient conditions. In particular, hydrolyzable compounds, e.g., alkoxides, of the desired elements of the pillars may be utilized as the precursors. Suitable polymeric silica precursor materials include tetraalkylsilicates, e.g., tetrapropylorthosilicate, tetramethylorthosilicate and, most preferably, tetraethylorthosilicate. Suitable polymeric silica precursor materials also include quaternary ammonium silicates, e.g., tetramethylammonium silicate (i.e., TMA silicate). Where the pillars also include polymeric alumina, a hydrolyzable aluminum compound can be contacted with the organic "propped" species before, after or simultaneously with the contacting of the propped layered oxide with the silicon compound. Preferably, the hydrolyzable aluminum compound employed is an aluminum alkoxide, e.g., aluminum isopropoxide. If the pillars are to include titania, a hydrolyzable titanium compound such as titanium alkoxide, e.g., titanium isopropoxide, may be used.

After calcination to remove the organic propping agent, the final pillared product may contain residual exchangeable cations. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

Particular procedures for intercalating layered materials with metal oxide pillars are described in U.S. Pat. Nos. 4,831,005; 4,831,006; and 4,929,587. The entire disclosures of these patents are expressly incorporated herein by reference. U.S. Pat. No. 4,831,005 describes plural treatments with the pillar precursor. U.S. Pat. No. 4,929,587 describes the use of an inert atmosphere, such as nitrogen, to minimize the formation of extralaminar polymeric oxide during the contact with the pillar precursor. U.S. Pat. No. 4,831,006 describes the use of elevated temperatures during the formation of the pillar precursor.

The resulting pillared products exhibit thermal stability at temperatures of 450° C. or even higher as well as substantial sorption capacities (as much as 17 to 40 wt % for $C_6$ hydrocarbon). The pillared products may possess a basal spacing of at least about 32.2A and surface areas greater than 500 $m^2/g$.

The layered material may be subjected to thermal treatment, e.g., to decompose organoammonium ions. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience.

Prior to its use as an alkylation catalyst, the MCM-36 should be subjected to thermal treatment to remove part or all of any organic constituent present therein.

The present catalyst may comprise MCM-36 in intimate combination with an optional hydrogenating component such as tungsten, vanadium, molybdenum, rhenium, nickel, cobalt, chromium, manganese, or a noble metal such as platinum or palladium. MCM-36 can also optionally be used in intimate combination with a rare earth component such as lanthanum or cerium. Such components can be associated chemically and/or physically with the MCM-36 and/or matrix with which the MCM-36 may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the MCM-36 such as, for example, by, in the case of platinum, treating the MCM-36 with a solution containing the platinum metal-containing ion. Thus, suitable platinum compounds for this purpose include chloroplatinic acid, platinous chloride and various compounds containing the platinum amine complex.

The MCM-36, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use as a catalyst in the present process, the MCM-36 crystals may be at least partially dehydrated. This dehydration can be accomplished by heating the MCM-36 to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the MCM-36 in a vacuum but a longer time will be required to achieve a suitable degree of dehydration.

The MCM-36 can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate the MCM-36 with another material, i.e., a binder, which is resistant to the temperatures and other conditions employed in the isoparaffin alkylation process of this invention. Suitable binder materials include active and inactive materials and synthetic or naturally occurring zeolites as well as inorganic materials such as clays, silica and/or metal oxides such as alumina. The latter can be either naturally occurring or provided in the form of gelatinous precipitates or gels including mixtures of silica and metal oxides. Use of a binder material in conjunction with MCM-36, i.e., combined therewith or present during its synthesis, which itself is catalytically active may change the conversion and/or selectivity of the catalyst. Inactive materials suitably serve as diluents to control the amount of conversion so that products can be obtained economically and in a controlled fashion without having to employ other means for controlling the rate of reaction. These materials can be incorporated into naturally occurring clays, e.g., bentonite and kaolin, to improve the crush strength of the MCM-36 under commercial operating conditions. Good crush strength is an advantageous attribute for commercial use since it prevents or delays breaking down of the catalyst into powder-like materials.

Naturally occurring clays which can be composited with MCM-36 crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with MCM-36 also include inorganic oxides, notably alumina.

Apart from or in addition to the foregoing binder materials, the MCM-36 crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may be advantageous to provide at least a part of the foregoing matrix materials in colloidal form so as to facilitate extrusion of the bound catalyst component(s).

The relative proportions of finely divided MCM-36 and inorganic oxide matrix can vary widely with the MCM-36 content ranging from about 1 to about 95 percent by weight and more usually, particularly when the composite is prepared in the form of beads, in the range of about 2 to about 80 weight percent of the composite.

The process of this invention can be carried out as a batch-type, semi-continuous, or continuous operation utilizing a fixed, fluidized or moving-bed catalyst system.

The feedstock is contacted with the present catalyst in the presence or absence of added hydrogen at elevated temperature and pressure. Temperatures may be from about 93° C. (200° F.) to 371° C. (700° F.), preferably from about 204° C. (400° F.) to 316° C. (600° F.). Because cracking reactions tend to increase with increasing temperatures, lower temperatures will normally be preferred in order to favor isomerization and/or disproportionation over the cracking reactions. Pressures may range from atmospheric up to 2000 psig. A particular range is from 50 to 1000 psig. Weight hourly space velocity may be from 0.1 to 50 $hr^{-1}$, more usually 0.2 to 10 $hr^{-1}$. If additional hydrogen is cofed with the feedstock, the hydrogen:feedstock molar ratio is generally from 0.1:1 to 10:1.

The process is preferably carried out in the presence of hydrogen, both to inhibit aging and to promote the isomerization reactions which are thought to proceed through an unsaturated intermediate.

The conversion may be conducted by contacting the feedstock with a fixed stationary-bed of catalyst, a fixed fluidized-bed, or with a transport bed. A simple configuration is a trickle-bed operation in which the feed is allowed to trickle through a stationary fixed bed. With such a configuration, it is desirable to initiate the reaction with fresh catalyst at a moderate temperature which is raised if the catalyst ages, in order to maintain catalytic activity. The catalyst may be regenerated by contact at elevated temperature with hydrogen gas, for example, or by burning in air or other oxygen-containing gas.

EXAMPLE 1

Preparation of Catalyst

A mixture of 258 grams of water, 20.5 grams of sodium aluminate solution (containing 25.5% $Al_2O_3$ and 19.5% $Na_2O$), 51.4 grams of precipitated silica (Ultrasil VN3), and 50 grams of hexamethyleneimine was reacted in a 600 ml autoclave at 154° C. for 136 hours with 400 rpm. The product was filtered and washed with water.

Part of the above wet cake (150 grams, 18% solids) was combined with 750 ml of a 29% solution of cetyltrimethylammonium chloride/hydroxide (obtained by contacting the chloride with a hydroxide-for-chloride ion exchange resin) and heated in the steambox for 20 hr. After filtration, washing with water, and air drying, the solid was reacted with a tetramethylammonium silicate solution (10% $SiO_2$, molar ratio TMA/Si=0.5), at a weight ratio 1:6, in a steambox for 20 hours. The product was filtered and air dried. It was mixed with alumina (35% content of alumina based on solids) and exchanged 3 times with 1M ammonium nitrate solution. The final product was obtained upon calcination at 450° C. in nitrogen for 3 hours followed by a 6 hour calcination in air at 540° C.

EXAMPLE 2

Paraffin Reactions

A fixed-bed reactor was employed to scope process conditions. The reactor was operated at 900 psig, at temperatures between 232° C. and 371° C., with feed rates of 1 hr⁻¹ to 4 hr⁻¹ WHSV. Approximately 4.5 grams of catalyst was loaded into the reactor. The catalyst was dried for 3 hours in flowing $N_2$ (150 cc/min) at 315° C. and 900 psig. Following the drying cycle, the reactor temperature was lowered to 232° C. After thermal equilibrium was reached, the feed (isopentane) was introduced into the reactor. Products were analyzed using a Hewlett Packard 5890 gas chromatograph with a 60 meter DB-1 column and FID detector.

TABLE 9-continued

Process Conditions and Product Selectivities for the Conversion of Isopentane over MCM-36

| Run | 1 | 2 | 3 | 4 |
|---|---|---|---|---|
| i-$C_5$ | 16.2 | 18.8 | 12.9 | 19.7 |
| $C_6$ | 38.8 | 43.3 | 38.6 | 45.7 |
| $C_7$ | 3.7 | 2.3 | 3.6 | 2.7 |
| $C_8$ | 0.6 | 1.1 | 2.3 | 0.0 |
| $C_6+$ | 43.1 | 46.7 | 44.5 | 48.4 |

TABLE 10

Comparison of Product Selectivities Obtained Over MCM-36 and ZSM-5 - isopentane Feed, 900 Psig and 1 WHSV

| | | | Product Selectivity | | | | | $C_6+$ Properties | | | |
|---|---|---|---|---|---|---|---|---|---|---|---|
| Catalyst | Conv | Temp | $C_3-$ | $C_4$ | $iC_4$ | $nC_5$ | $C_6+$ | Iso/normal | R + M/2 | RVP | % Aromatics |
| MCM-36 | 26.8 | 500 | 3.9 | 36.7 | 35.4 | 16.2 | 43.1 | 23 | 80.5 | 6.2 | 0.0 |
| ZSM-5 | 21.0 | 500 | 11 | 39.6 | 19.7 | 23.4 | 25.9 | 2.3 | 63 | 3.7 | 13.0 |

The results of the conversion of iso-pentane over MCM-36 are shown in Table 9. These results show that conversions as high as ~50 wt % conversion (at 288° C., 1 WHSV, and 900 psig) are possible with ~45 wt % selectivity to $C_6+$ products. Selectivity to isomerized product is less than 15 wt %, with ~40 wt % selectivity to butanes, predominately isobutane, which is useful as a paraffin-olefin alkylation feed. A comparison of the conversion and selectivity data obtained over MCM-36 to data obtained over another catalyst is shown in Table 10. This table shows that MCM-36 is as active in terms of feed conversion as ZSM-5.

The $C_6+$ product selectivity obtained over MCM-36 demonstrates a high $C_6+$ iso/normal ratio. The $C_6+$ selectivity and iso/normal ratio obtained over MCM-36 is higher than that obtained over ZSM-5, resulting in higher $C_6+$ octanes and lower recycle in a commercial process. Additionally, high isobutane selectivity is obtained over MCM-36 (35 wt %) relative to ZSM-5 (20 wt %) with minimum selectivity to light $C_3-$ and isomerate.

The $C_6+$ product synthesized over MCM-36 is free of aromatics and olefins, with an octane (R+M/2) of ~80 and RVP of ~6 psi. At the same conversion level, ~13 wt % $C_6+$ aromatics are synthesized over ZSM-5. Despite this high level of aromatics, the octane (R+M/2) of the $C_6+$ product synthesized over ZSM-5 is only 63, due to the low iso/normal of the $C_6+$ paraffins.

TABLE 9

Process Conditions and Product Selectivities for the Conversion of Isopentane over MCM-36

| Run | 1 | 2 | 3 | 4 |
|---|---|---|---|---|
| Temp, °C. | 260 | 260 | 288 | 288 |
| Pressure, psig | 900 | 900 | 900 | 900 |
| WHSV, hr⁻¹ | 1 | 1 | 1 | 2 |
| Conversion, % | 26.8 | 17.9 | 47.2 | 24.3 |
| Selectivity, wt % | | | | |
| $C_1-C_2$ | 0.3 | 0.2 | 0.2 | 0.3 |
| $C_3$ | 3.6 | 2.7 | 3.8 | 2.7 |
| $C_4$ (Total) | 36.7 | 31.4 | 38.5 | 28.9 |
| i-$C_4$ | 35.4 | 30.3 | 35.5 | 27.3 |
| $C_5$ (Total) | 16.3 | 19.0 | 13.0 | 19.7 |

What is claimed is:

1. A process for disproportionating a paraffin having from 3 to 10 carbon atoms, said process comprising contacting said paraffin with a catalyst comprising MCM-36, said contacting taking place under conditions sufficient to cause a disproportionation reaction involving conversion of said paraffin to other paraffins having at least one more or at least one less carbon atoms per molecule.

2. A process according to claim 1, wherein the reaction conditions include a temperature of from about 93° C. to 371° C., a pressure of from atmospheric to 2000 psig, and a weight hourly space velocity of from 0.1 to 50 hr⁻¹.

3. A process according to claim 1, wherein said catalyst further comprises a hydrogenation metal.

4. A process according to claim 3, wherein hydrogen is cofed along with paraffin feedstock and contacted with said catalyst.

5. A process according to claim 4, wherein the molar ratio of cofed hydrogen to paraffin feedstock is from 0.1:1 to 10:1.

6. A process according to claim 3, wherein said hydrogenation metal is platinum.

7. A process according to claim 1, wherein isopentane is disproportionated to a product comprising isobutane and branched hexanes.

8. A process according to claim 1, wherein the layers of the MCM-36 have a composition comprising the molar relationship $X_2O_3$:(n)$YO_2$, wherein n is at least about 5, X is a trivalent element, and Y is a tetravalent element.

9. A process according to claim 8, wherein X is selected from the group consisting of aluminum, boron, gallium, and combinations thereof; and Y is selected from the group consisting of silicon, germanium, and combinations thereof.

10. A process according to claim 8, wherein X comprises aluminum and Y comprises silicon.

11. A process according to claim 1, wherein hydrogen is cofed along with paraffin feedstock and contacted with said catalyst.

12. A process according to claim 11, wherein said catalyst does not comprise a hydrogenation metal.

* * * * *